US00PP33654P2

(12) United States Plant Patent
Volz

(10) Patent No.: US PP33,654 P2
(45) Date of Patent: Nov. 23, 2021

(54) APPLE TREE NAMED 'PREMA093'

(50) Latin Name: *Malus domestica*
Varietal Denomination: PremA093

(71) Applicant: Prevar Limited, Hastings (NZ)

(72) Inventor: Richard Volz, Auckland (NZ)

(73) Assignee: Prevar Limited, Hastings (NZ)

( * ) Notice: Subject to any disclaimer, the term of this patent is extended or adjusted under 35 U.S.C. 154(b) by 0 days.

(21) Appl. No.: 16/873,562

(22) Filed: May 4, 2020

(30) Foreign Application Priority Data

Jul. 29, 2019 (NZ) ..... 34596

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 5/0875
See application file for complete search history.

*Primary Examiner* — Kent L Bell
(74) *Attorney, Agent, or Firm* — Michelle Bos Legal LLC

(57) ABSTRACT

A new and distinct apple tree named 'PremA093', the fruit of which is notable for its intense red skin color and early maturity.

5 Drawing Sheets

Latin name: *Malus domestica.*
Variety denomination: 'PremA093'.

BACKGROUND OF THE VARIETY

The new apple tree variety 'PremA093' was created in the course of a planned breeding program carried out at Havelock North, New Zealand. 'PremA093' originated as a result of a controlled cross made in 2001 of 'Scifresh' (seed parent, U.S. Plant Pat. No. 13,888) and 'A080R12T094' (pollen parent, not patented). 'PremA093' was selected as a single plant from among a population of seedlings derived from the parents, and was initially selected for its intense red skin color and early maturity as compared to 'Galaxy' Gala (U.S. Plant Pat. No. 6,955). The variety has been observed over a number of asexually propagated generations, and has been found to remain true to type.

'PremA093' is easily distinguished from late-maturing male parent 'A080R12T094', the fruit of which is yellow-green with little to no blush overcolor as compared to the intense red skin color of 'PremA093'. The male parent produces globose conical fruit as compared to the ovoid to conical fruit of 'PremA093'. 'PremA093' is distinguished from female parent 'Scifresh' and from similar varieties 'Galaxy' Gala and 'PremA280' (U.S. Plant Pat. No. 19,762) as set forth in Table 1 below.

TABLE 1

Comparison of 'PremA093' to female parent and other varieties

| | 'PremA093' | 'Scifresh' | 'Galaxy' | 'PremA280' |
|---|---|---|---|---|
| Maturity date | Very early | Mid-season | Early | Early |
| Pattern of skin color | Solid flush | Striped | Striped | Striped |
| Overcolor | Red-purple | Red with greyed-red stripes | Cherry red | Greyed-red |
| Flavor acidity | Sweet/acid | Sweet/medium | Sweet/mild | Sweet/mild |

BRIEF DESCRIPTION OF THE PHOTOGRAPHS

The attached photographs were taken at Napier, New Zealand in 2020, of 5-year-old trees and their fruit. The trees were grown on 'M116' rootstock (U.S. Plant Pat. No. 18,618).

Figure 1:
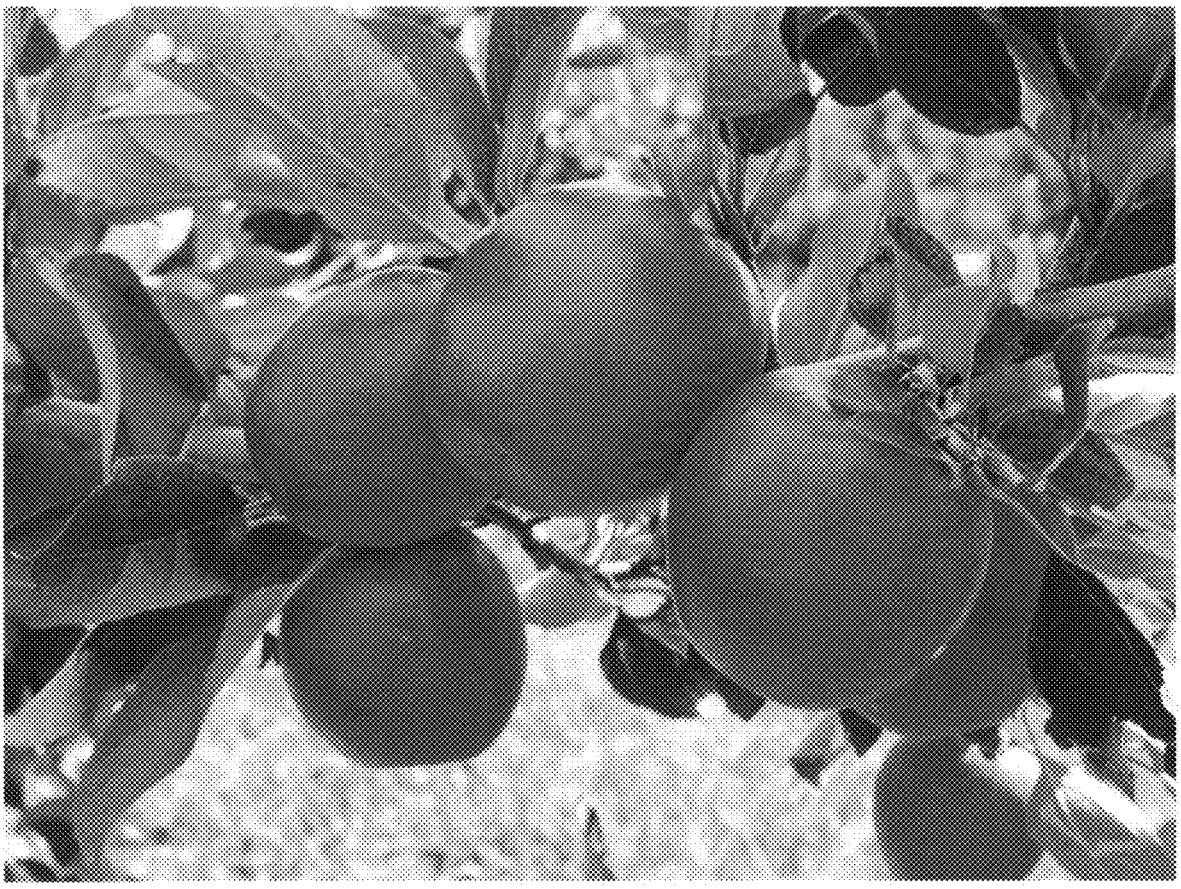
Figure 2:
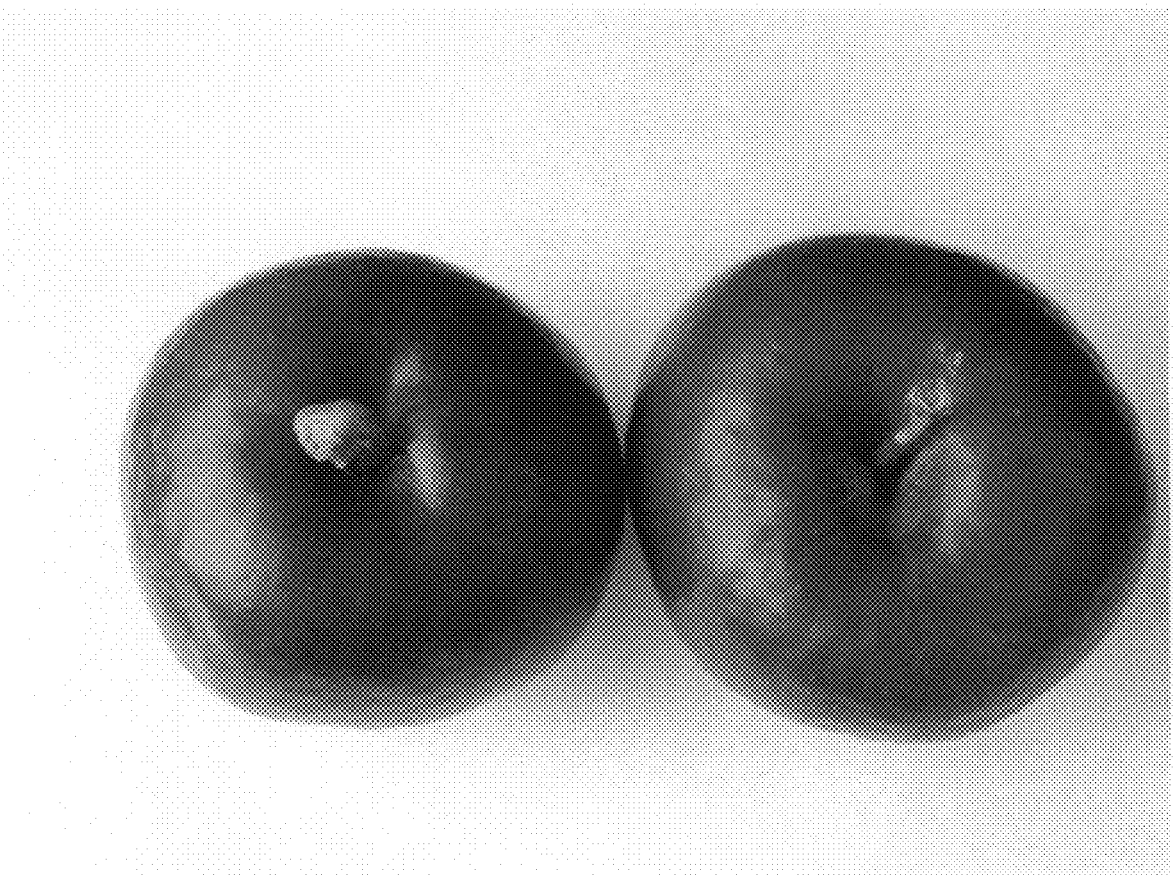
Figure 3:
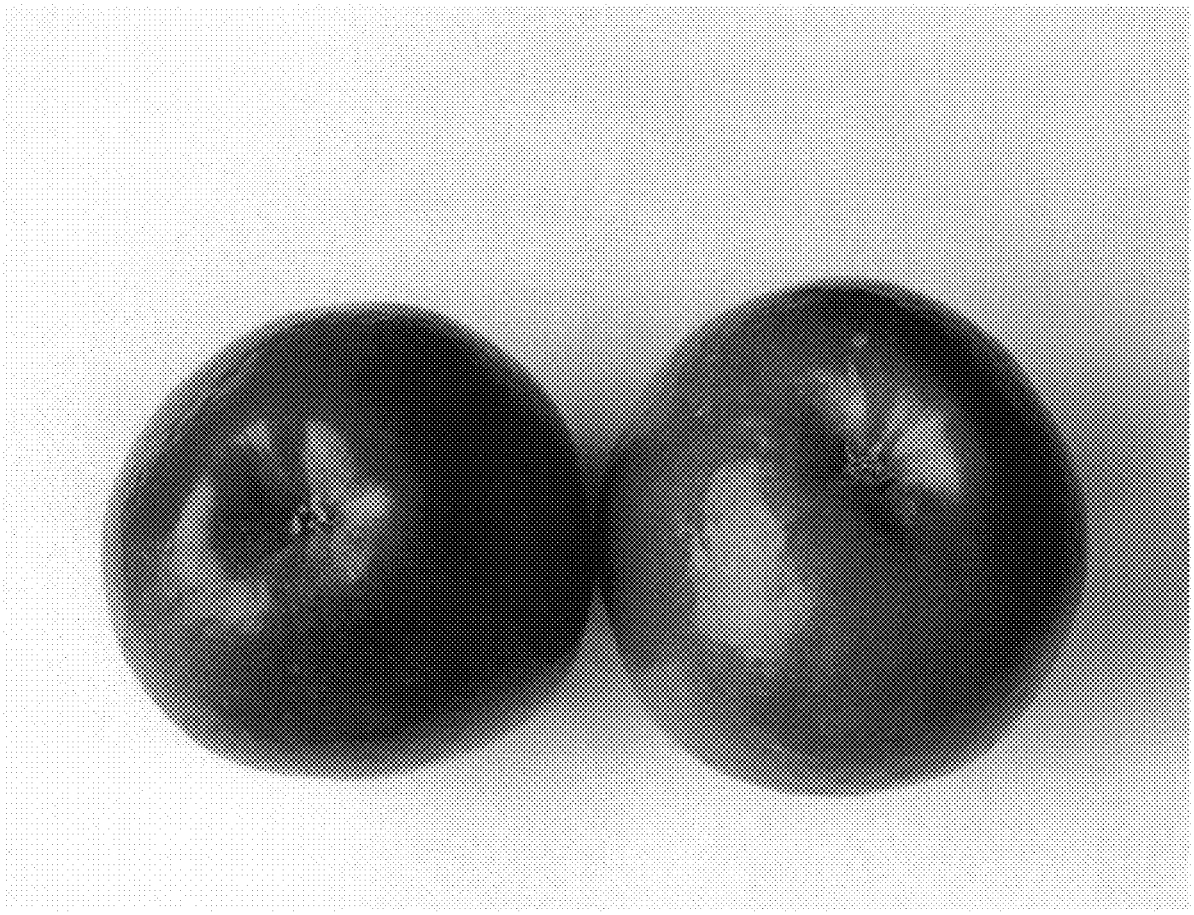
Figure 4:
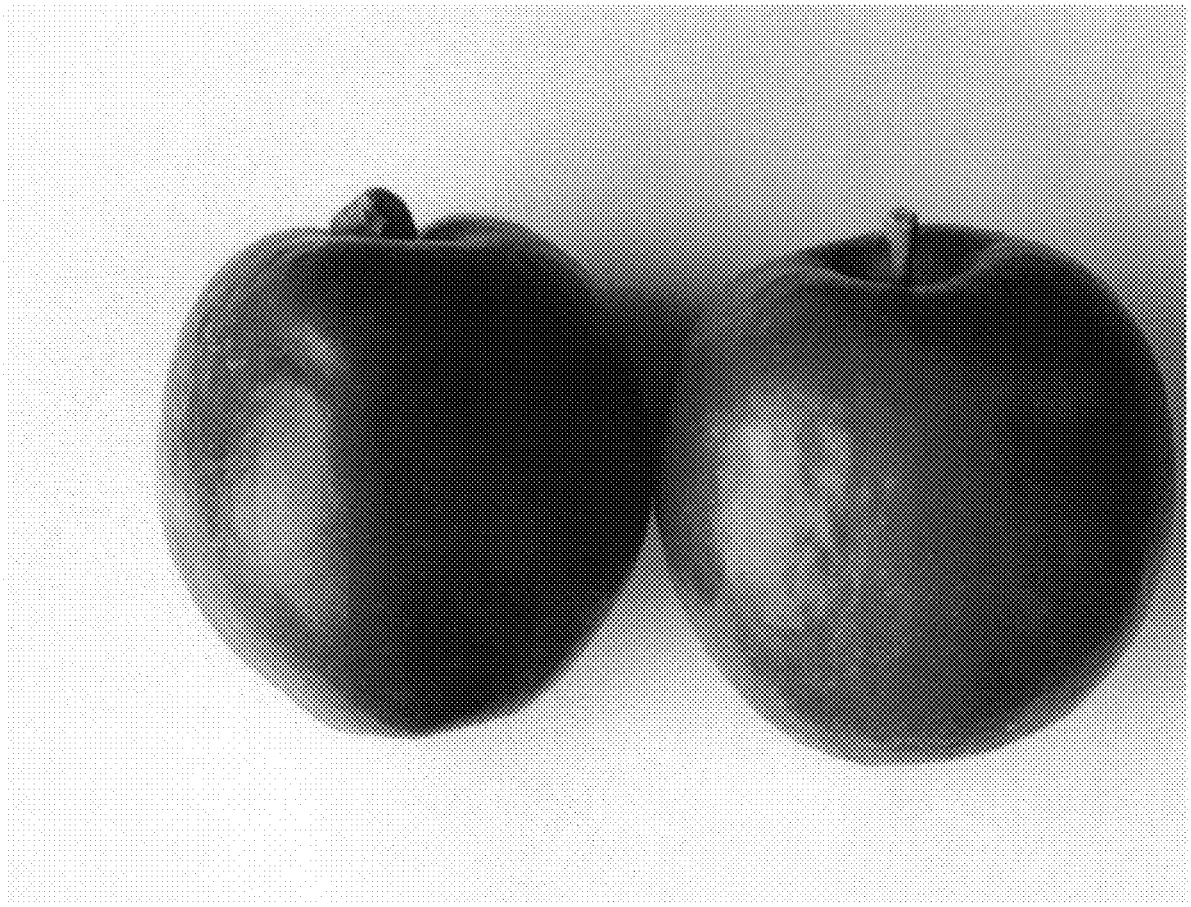
Figure 5:
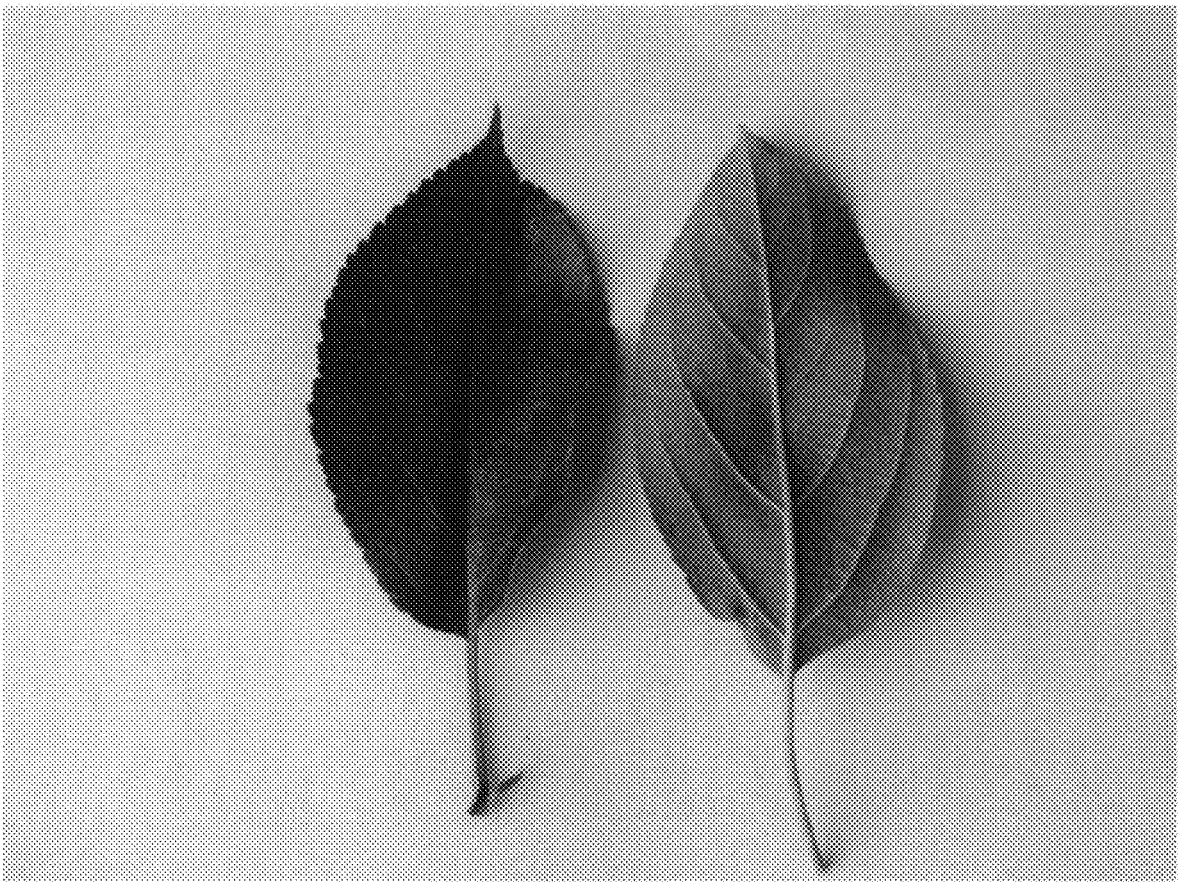

FIG. 1 shows the fruit, branches and leaves of the variety;
FIG. 2 shows a stem-end view of fruit of the variety;
FIG. 3 shows a calyx-end view of fruit of the variety;
FIG. 4 shows a side view of fruit of the variety; and
FIG. 5 shows leaves of the variety.

DETAILED BOTANICAL DESCRIPTION OF THE VARIETY

The following-detailed botanical description is based on observations of 5-year-old trees made during the 2019-2020 growing season at Napier, New Zealand, except where otherwise noted. The described trees were grown on 'M116' rootstock. All colors are described according to The Royal Horticultural Society Colour Chart. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:

*Vigor.*—Moderate.
*Type.*—Ramified.
*Habit.*—Spreading.
*Height.*—2.4 to 3 meters.
*Spread.*—1.5 m.
*Trunk diameter* (*at* 30 *cm above the graft*).—50 to 74 cm.
*Bark color.*—Brown N200C.
*Bark texture.*—Smooth.

*Lenticel length.*—2 mm to 5 mm.
*Lenticel width.*—0.8 to 1.0 mm.
*Lenticel height.*—Flush to slightly raised.
*Lenticel shape.*—Elongated.
*Lenticel color.*—Grey-brown 199C.
*Lenticel density.*—Dense, about 3 per $cm^2$.

Branch (fruiting branches located at around 1 m above the graft union):
*Length.*—1 to 1.3 meters.
*Diameter.*—23 to 30 mm.
*Bark color.*—Brown N200C.
*Bark texture.*—Smooth.
*Branch lenticel length.*—2 to 3 mm.
*Branch lenticel width.*—0.5 to 0.8 mm.
*Lenticel height.*—Flush to slightly raised.
*Branch lenticel shape.*—Elongated.
*Branch lenticel color.*—Grey-brown 199C.
*Branch lenticel density.*—3 to 5 per $cm^2$.

One year old shoot:
*Length.*—15 to 30 cm.
*Diameter.*—4 to 5 mm.
*Color.*—Brown 200A.
*Pubescence.*—Light.
*Internode length.*—2.3 to 2.7 mm.
*Shoot lenticel length.*—0.5 to 1 mm.
*Shoot lenticel width.*—0.5 mm.
*Shoot lenticel height.*—Flush.
*Shoot lenticel shape.*—Oval.
*Shoot lenticel color.*—Grey 201B.
*Shoot lenticel density.*—3 to 7 per $cm^2$.

Flower buds (bud and bloom observations recorded near Yakima, Wash., USA):
*Number per spur.*—4 to 5.
*Shape.*—Elongated with pointed apex.
*Length.*—12 mm.
*Diameter.*—8 mm.
*Texture.*—Smooth.
*Color.*—Red-purple 58B.

Flowers:
*First bloom.*—Early, April 16 (2021 growing season).
*Full bloom.*—Early, April 20 (2021 growing season).
*Pollination requirement.*—Required.
*Quantity per cluster.*—4 to 5.
*Diameter.*—45 mm.
*Depth.*—2 mm.
*Fragrance.*—Fragrant, typical.

Petals:
*Quantity per flower.*—5.
*Length.*—20 mm.
*Width.*—17 mm.
*Shape.*—Oval.
*Apex.*—Pointed.
*Base.*—Rounded.
*Margin.*—Smooth.
*Texture of upper surface.*—Smooth.
*Texture of lower surface.*—Smooth to mildly rugulose.
*Color of upper surface.*—White N155C with red-purple N57D.
*Color of lower surface.*—White N155B with red-purple N57C.

Pistils:
*Quantity.*—3 to 4.
*Length.*—7 mm.
*Color.*—Yellow 1D.
*Stigma diameter.*—1 mm.
*Stigma color.*—Yellow 3C.
*Style diameter.*—1 mm.
*Style color.*—Yellow 2D.
*Ovary diameter.*—5 mm.
*Ovary length.*—7 mm.
*Ovary color.*—Green 141B.

Stamens:
*Quantity.*—14.
*Anther length.*—2 mm.
*Anther width.*—1 mm.
*Anther color.*—Yellow 6D.
*Filament length.*—7 mm.
*Filament color.*—Yellow 2D.
*Pollen.*—Moderately abundant, yellow 6D.

Pedicel:
*Length.*—24 mm.
*Diameter.*—2 mm.
*Texture.*—Smooth.
*Color.*—Yellow-green 145B.

Sepals:
*Quantity.*—5.
*Length.*—10 mm.
*Width.*—3 mm.
*Shape.*—Pointed.
*Margin.*—Smooth.
*Texture of upper surface.*—Smooth.
*Texture of lower surface.*—Smooth.
*Color of upper surface.*—Yellow-green 145A.
*Color of lower surface.*—Yellow-green 145B.

Leaves:
*Shape.*—Ovate.
*Length.*—90 to 100 mm.
*Width.*—47 to 52 mm.
*Length/width ratio.*—2:1.
*Blade margin.*—Crenate.
*Apex.*—Acuminate.
*Base shape.*—Equilateral.
*Texture of upper surface.*—Glabrous.
*Texture of lower surface.*—Glabrous with prominent veins.
*Color of upper surface.*—Green 137A.
*Color of lower surface.*—Green 138B.
*Attitude in relation to shoot.*—Upward.

Petiole:
*Length.*—30 to 41 mm.
*Diameter.*—1.8 to 1.9 mm.
*Color.*—Green 137C.

Fruit:
*Quantity per cluster.*—4.
*Diameter.*—68 to 79 mm.
*Height.*—72 to 82 mm.
*Weight.*—140 to 243 g.
*General shape in profile.*—Conic to ovoid.
*Position of maximum diameter.*—At or above equator.
*Ribbing.*—None.
*Crowning at calyx end.*—Slight.
*Size of eye.*—Small.
*Aperture of eye.*—Partially to fully open.
*Depth of eye basin.*—5.7 to 7.1 mm.
*Width of eye basin.*—24 to 26 mm.
*Length of sepal.*—4 to 6 mm.
*Bloom of skin.*—Light.
*Greasiness of skin.*—Light.
*Background color of skin.*—Yellow 11C.

*Amount of over color.*—95% to 100%.
*Over color of skin.*—Red-purple 59A and 59B.
*Intensity of over color.*—Intense.
*Pattern of over color.*—Solid flush.
*Amount of russet around stalk cavity.*—Low.
*Amount of russet on cheeks.*—None.
*Area of russet around eye basin.*—Low.
*Length of stalk.*—19 to 21 mm.
*Thickness of stalk.*—2.1 to 4 mm.
*Depth of stalk cavity.*—13 to 14.5 mm.
*Width of stalk cavity.*—24 to 38 mm.
*Stalk color.*—Greyed-orange 175B.
*Firmness of flesh.*—Firm.
*Flesh texture.*—Fine.
*Aroma.*—Slight.
*Juiciness.*—Juicy.
*Brix.*—12.6 to 13.1° Brix.
*Flesh color.*—White 155A.
*Quantity of locules.*—5.
*Aperture of locules.*—Closed to slightly open.

Seeds:
*Quantity per fruit.*—10.
*Shape.*—Teardrop.
*Length.*—9.0 to 9.6 mm.
*Width.*—5.1 to 6.0 mm.
*Color.*—Greyed-orange 175A.

Harvest:
*Time for harvest.*—Beginning February 1; 8 to 15 days before. 'Galaxy' (2018, Hawkes Bay, NZ).
*Harvest yield.*—About 31 kg per tree.
*Number of picks.*—Two.
*Disease susceptibility.*—Moderately susceptible to fire blight.
*Storage characteristics.*—Slow cooling after harvest prevents soft scald.
*Market use.*—Fresh local market and export.
*Eating quality.*—Very good.

I claim:

1. A new and distinct apple tree substantially as described and illustrated herein.

* * * * *